US008827922B2

(12) United States Patent
Aoki et al.

(10) Patent No.: US 8,827,922 B2
(45) Date of Patent: Sep. 9, 2014

(54) ENDOSCOPE APPARATUS

(75) Inventors: Hidemichi Aoki, Tokorozawa (JP); Sunao Sato, Yamato (JP)

(73) Assignee: Olympus Medical Systems Corp., Tokyo (JP)

( * ) Notice: Subject to any disclaimer, the term of this patent is extended or adjusted under 35 U.S.C. 154(b) by 970 days.

(21) Appl. No.: 12/490,593

(22) Filed: Jun. 24, 2009

(65) Prior Publication Data

US 2009/0318831 A1 Dec. 24, 2009

(30) Foreign Application Priority Data

Jun. 24, 2008 (JP) ................................. 2008-164812

(51) Int. Cl.
*A61B 10/00* (2006.01)

(52) U.S. Cl.
USPC ........... 600/566; 600/104; 600/106; 600/160; 600/463

(58) Field of Classification Search
USPC ......... 600/103, 104, 106, 146, 160, 462, 463, 600/464, 566
See application file for complete search history.

(56) References Cited

U.S. PATENT DOCUMENTS

| 6,238,336 | B1 | 5/2001 | Ouchi | |
|---|---|---|---|---|
| 6,338,717 | B1 | 1/2002 | Ouchi | |
| 2007/0197871 | A1* | 8/2007 | Geitz et al. | 600/117 |
| 2007/0232922 | A1* | 10/2007 | Kohno | 600/459 |

FOREIGN PATENT DOCUMENTS

| DE | 199 29 314 A1 | 12/1999 |
|---|---|---|
| DE | 199 39 109 A1 | 2/2000 |
| DE | 199 62 209 A1 | 6/2000 |
| JP | 2000-185042 | 7/2000 |
| JP | 2004-154300 | 6/2004 |

* cited by examiner

*Primary Examiner* — Long V. Le
*Assistant Examiner* — Bo J Peng
(74) *Attorney, Agent, or Firm* — Scully, Scott, Murphy & Presser, P.C.

(57) ABSTRACT

An endoscope apparatus according to the present invention includes an insertion portion having a distal end portion and at least two channels; an optical observation system provided on one surface of the distal end portion so as to face an axial direction different from a direction of an insertion axis X of the insertion portion; a first channel opening provided on one surface of the distal end portion near the optical observation system; an ultrasound transducer array provided on the one surface of the distal end portion and having a scanning surface Z parallel to the insertion axis; and a second channel opening provided on a proximal end side of the ultrasound transducer array.

4 Claims, 5 Drawing Sheets

ENDOSCOPE APPARATUS

This application claims benefit of Japanese Application No. 2008-164812 filed in Japan on Jun. 24, 2008 the contents of which are incorporated by this reference.

BACKGROUND OF THE INVENTION

1. Field of the Invention

The present invention relates to an endoscope apparatus that can alone perform endoscopic ultrasound-guided fine needle aspiration biopsy and endoscopic retrograde cholangiopancreatography.

2. Description of the Related Art

As known, endoscope apparatuses have been widely used for observation and treatment of an inside of a living body (an inside of a body cavity) or inspection and repairs in industrial plant facilities. In recent years, medical endoscope apparatuses have been developed that can perform endoscopic ultrasound-guided fine needle aspiration biopsy (FNA) for checking pancreas and its surroundings in ultrasound images and collecting cells of the pancreas by puncture for pathological examination, or endoscopic retrograde cholangiopancreatography (ERCP) for inserting a thin tube through pancreatic duct or bile duct, injecting a contrast medium and checking by radiography to examine changes of the pancreatic duct or bile duct.

As such an endoscope apparatus, for example, Japanese Patent Application Laid-Open Publication No. 2000-185042 discloses a distal end portion of an ultrasound endoscope in which an annular ultrasound transducer array for radial scanning is provided in a distal end of an insertion portion, and a treatment instrument protrusion opening is provided on a distal side of the ultrasound transducer array, thereby preventing a treatment instrument from damaging a balloon provided around the ultrasound transducer array.

Also, for example, Japanese Patent Application Laid-Open Publication No. 2004-154300 discloses a distal end portion of an ultrasound endoscope in which an optical observation window and an ultrasound probe are provided in a distal end portion of an insertion portion, and a plurality of treatment instrument protrusion openings through which treatment instruments are protruded are arranged along a scanning surface of the ultrasound probe.

SUMMARY OF THE INVENTION

An endoscope apparatus according to the present invention includes: an insertion portion to be inserted into a body cavity and having a distal end portion and at least two treatment instrument channels; an optical observation system provided on one surface of the distal end portion so as to face an axial direction different from a direction of an insertion axis of the insertion portion; a first channel opening provided on the one surface of the distal end portion near the optical observation system; an ultrasound transducer array provided on the one surface of the distal end portion and having a scanning surface parallel to the insertion axis; and a second channel opening provided on a proximal end side of the ultrasound transducer array.

The above and other objects, features and advantages of the invention will become more clearly understood from the following description referring to the accompanying drawings.

DETAILED DESCRIPTION OF THE PREFERRED EMBODIMENT

Now, an embodiment of the present invention will be described with reference to the drawings. The present invention provides an embodiment of an endoscope apparatus that alone can perform endoscopic retrograde cholangiopancreatography (ERCP) and endoscopic ultrasound-guided fine needle aspiration biopsy (FNA).

Figure 1:
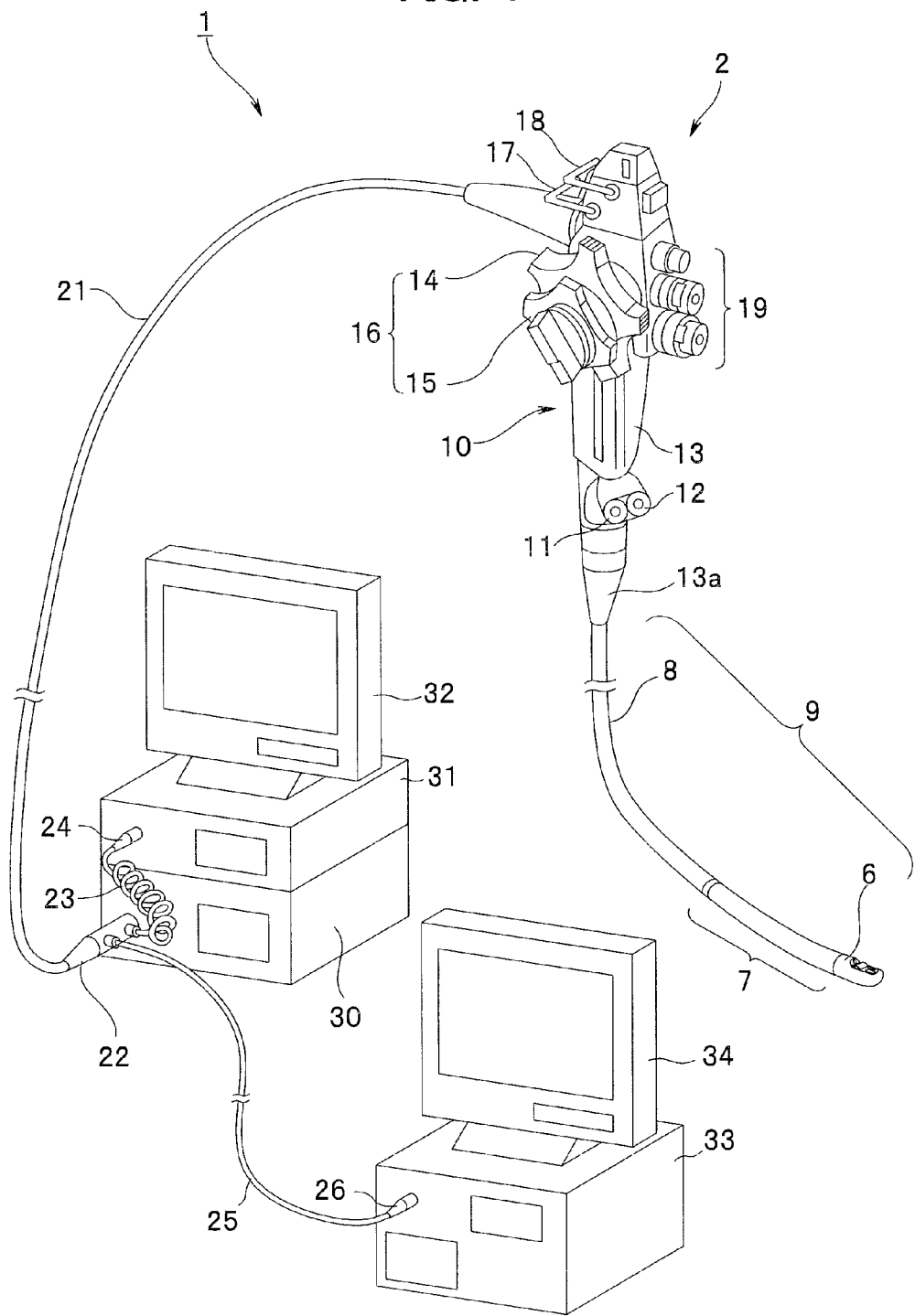
FIG. 1 is a view showing an entire configuration of an endoscopic ultrasound system of the present invention.
Figure 2:
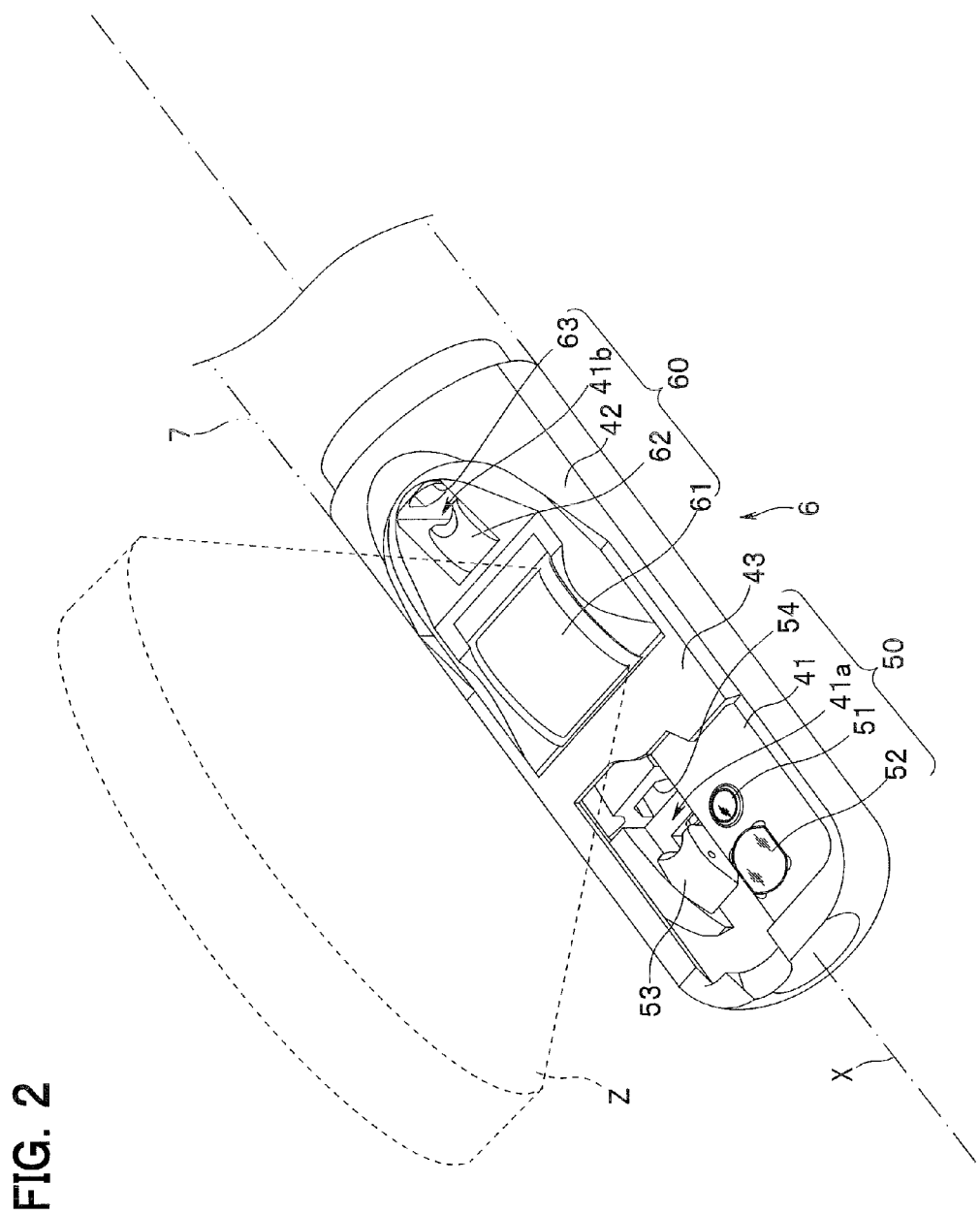
FIG. 2 is a perspective view of a configuration of a distal end portion of the endoscopic ultrasound system of the present invention.
Figure 3:
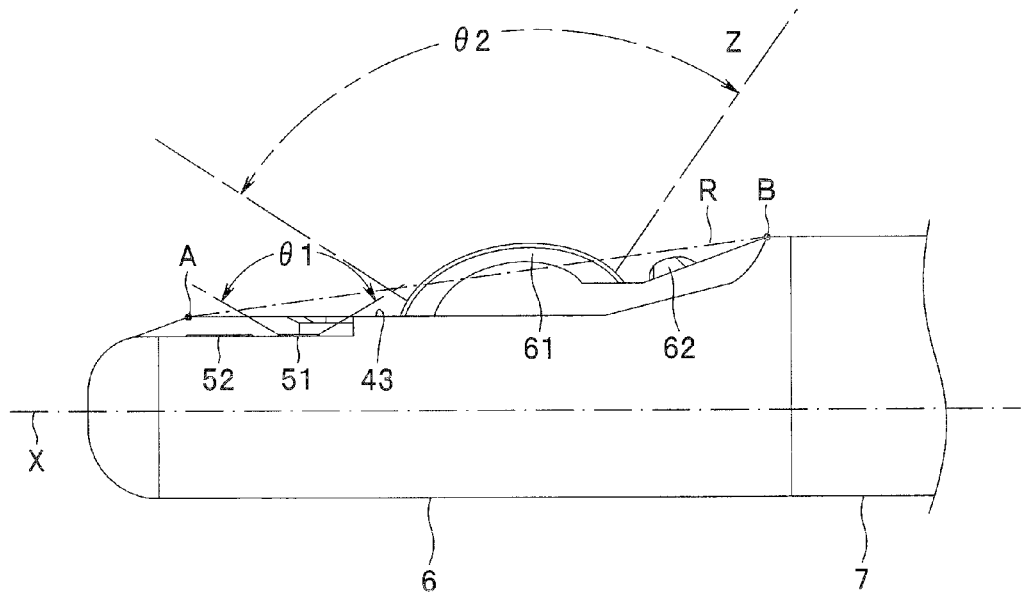
FIG. 3 is a side view of the configuration of the distal end portion of the endoscopic ultrasound system of the present invention.
Figure 4:
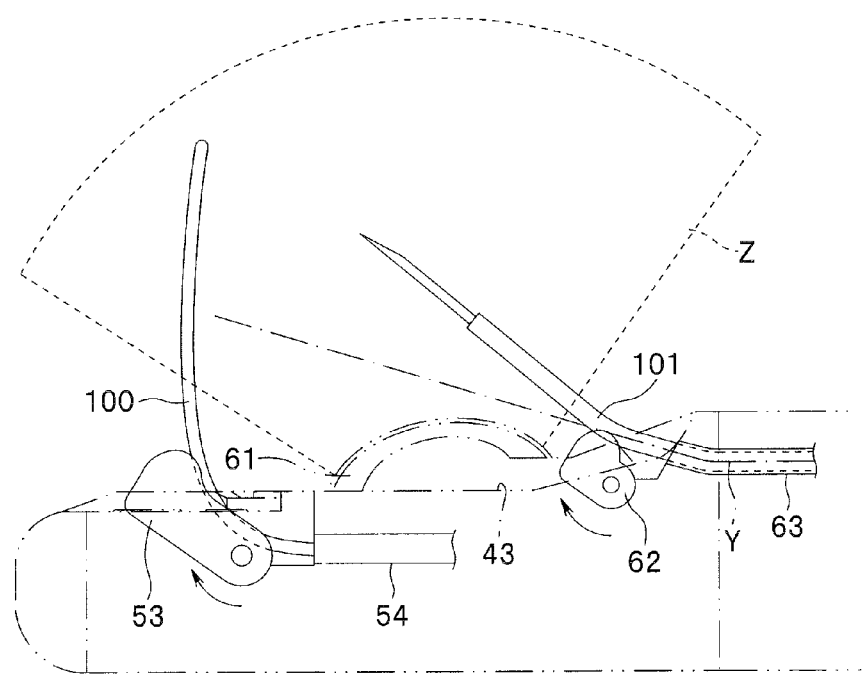
FIG. 4 is a side view of the distal end portion for illustrating a raising base of the endoscopic ultrasound system of the present invention.
Figure 5:
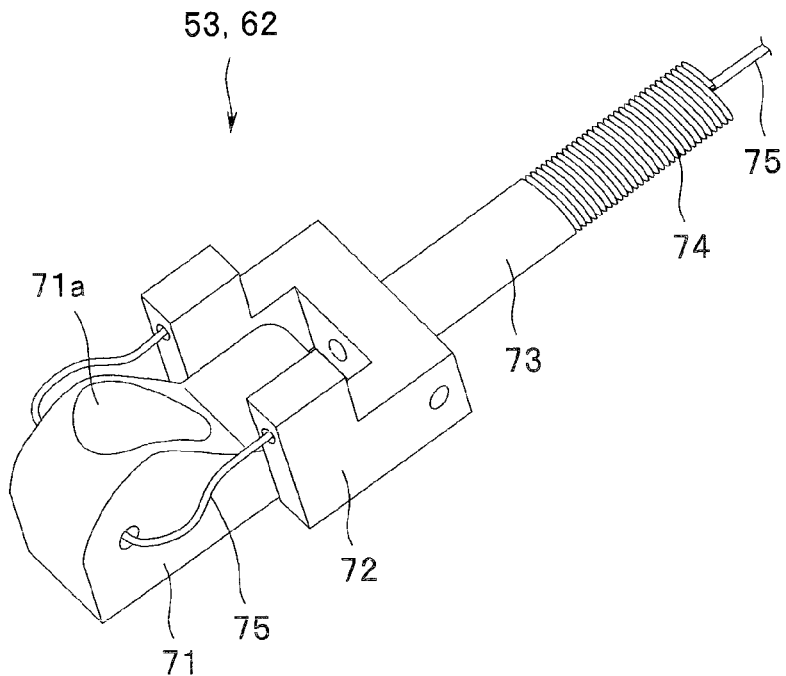
FIG. 5 is a perspective view of a configuration of the raising base of the endoscopic ultrasound system of the present invention.
Figure 6:
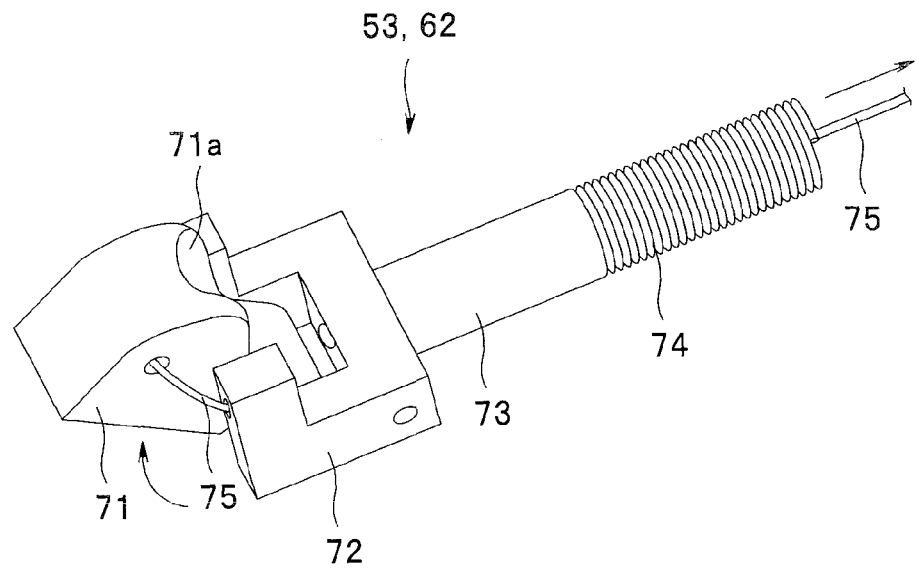
FIG. 6 is a perspective view of the raising base in a raised manner of the endoscopic ultrasound system of the present invention.
Figure 7:
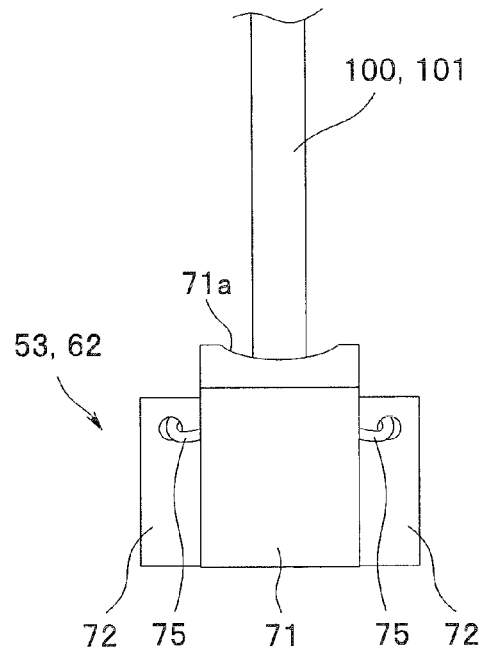
FIG. 7 is a front view of the raising base in the raised manner of the endoscopic ultrasound system of the present invention.
Figure 8:
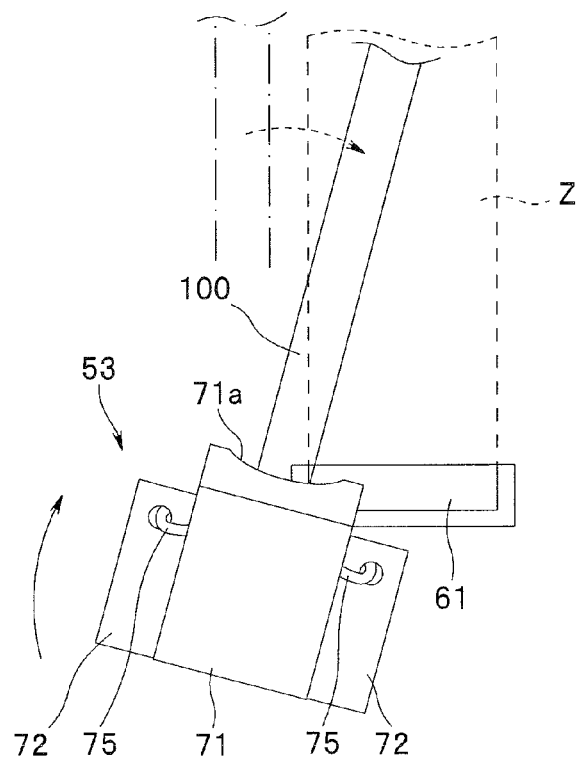
FIG. 8 is a view showing a configuration of a raising base of a variant of the endoscopic ultrasound system.

First, the present invention will be described with reference to FIGS. 1 to 6. FIGS. 1 to 6 relate to the embodiment of the present invention, FIG. 1 is a view showing an entire configuration of an endoscopic ultrasound system, FIG. 2 is a perspective view of a configuration of a distal end portion, FIG. 3 is a side view of the configuration of the distal end portion; FIG. 4 is a side view of the distal end portion for illustrating a raising base, FIG. 5 is a perspective view of a configuration of the raising base, FIG. 6 is a perspective view of the raising base in a raised manner, FIG. 7 is a front view of the raising base in the raised manner, and FIG. 8 is a view showing a configuration of a raising base of a variant.

As shown in FIG. 1, an endoscopic ultrasound system 1 of the present embodiment includes an endoscope apparatus (hereinafter simply referred to as an endoscope) 2, a light source device 30, a video processor 31, a color monitor 32 for observation images, an ultrasound observation device 33, and a second monitor 34 for ultrasound images electrically connected.

The endoscope 2 includes an insertion portion 9 and an operation portion 10 from which the insertion portion 9 extends, and a universal cord 21 extending from the operation portion 10 is connected via a scope connector 22 to the light source device 30. A coil-like scope cable 23 and an ultrasound signal cable 25 extend from the scope connector 22. An electric connector 24 is provided at the other end of the scope cable 23 and connected to the video processor 31. An ultrasound connector 26 is provided at the other end of the ultrasound signal cable 25 and connected to the ultrasound observation device 33.

The insertion portion 9 includes a distal end portion 6, a bending portion 7, and a flexible tube 8 connected in order from a distal end. A plurality of channel openings, an optical observation window, an optical illumination window, and an ultrasound transducer array or the like are provided on one side surface of the distal end portion 6, though not shown.

The operation portion 10 includes a bend preventing portion 13a from which the insertion portion 9 extends, a plurality of (two herein) forceps openings 11 and 12 provided on a lower side portion, an operation portion body 13 constituting a grip in a middle portion, a bending operation portion 16 including two bending operation knobs 14 and 15 provided over one upper surface of the operation portion body 13, a plurality of switches 19 for operating various endoscope functions and mainly operating an image pickup function, and two raising levers 17 and 18 for operating raising bases described later. The forceps openings 11 and 12 in the operation portion 10 constitute openings on the operator's side of two unshown treatment instrument channels mainly passing through the insertion portion 9 to two channel openings provided in the distal end portion 6.

Next, a configuration of the distal end portion 6 of the endoscope 2 will be described with reference to FIGS. 2 to 4.

As shown in FIGS. 2 to 4, the distal end portion 6 of the endoscope 2 includes a distal end rigid portion 41 of metal and a distal end cover 42 of synthetic resin covering the distal end rigid portion 41.

The distal end rigid portion 41 has two exposed portions on one surface 43 of the distal end cover 42 of the insertion portion 9 as a longitudinal axis of the distal end portion 6. One of the exposed portions of the distal end rigid portion 41 is an optical observation function unit 50, and the other is an ultrasound observation function unit 60.

The optical observation function unit 50 is located on a front side of the ultrasound observation function unit 60 along the insertion axis X. Specifically, the distal end portion 6 includes the optical observation function unit 50 and the ultrasound observation function unit 60 provided on front and rear sides along the insertion axis X on the one surface 43 facing a direction perpendicular to the insertion axis X.

The optical observation function unit 50 includes an optical observation window 51 that constitutes an optical observation system of an image pickup apparatus including an unshown solid-state image pickup device provided in the distal end portion 6, an optical illumination window 52 provided on a front side of the optical observation window 51 along the insertion axis X, a first raising base 53 pivotably provided so as to protrude from and retract into a first opening 41a constituting a channel opening formed in the distal end rigid portion 41 on a lateral position of the windows 51 and 52, and a first treatment instrument channel 54 opening in a rear surface of a recess constituting the first opening 41a.

An unshown image pickup apparatus included in the distal end portion 6 is provided on a back side of the optical observation function unit 50. Specifically, light in a direction perpendicular to the insertion axis is incident on the optical observation window 51, and the incident light is photoelectrically converted by the image pickup apparatus. The endoscope 2 of the present embodiment has a configuration including a side-viewing optical image pickup system with a predetermined viewing angle $\theta 1$ as shown in FIG. 3. Thus, the endoscope 2 has a configuration for observation performance of duodenal papilla in endoscopic retrograde cholangiopancreatography (ERCP).

An end surface of an unshown light guide bundle faces a back side of the optical illumination window 52, the light guide bundle passing through the universal cord 21 from the distal end portion 6 and transmitting illumination light from the light source device 30 (see FIG. 1). Specifically, the optical illumination window 52 is an optical member for applying, to a subject, illumination light applied from the end surface of the light guide bundle provided in the distal end portion 6.

The first raising base 53 is provided pivotably in the first opening 41a. The first raising base 53 is pivoted by an operation of the raising lever 17 (see FIG. 1) provided in the operation portion 10. The first raising base 53 is pivoted in a raised direction to raise and guide a treatment instrument, for example, a contrast tube 100 protruded from the first treatment instrument channel 54 into the first opening 41a in a direction perpendicular to the insertion axis X.

The ultrasound observation function unit 60 includes a convex ultrasound transducer array 61, a second raising base 62 provided on a rear side of the ultrasound transducer array 61 along the insertion axis X, and pivotably provided so as to protrude from and retract into a second opening 41b constituting a channel opening formed in the distal end rigid portion 41, and a second treatment instrument channel 63 opening in a rear surface of a recess constituting the second opening 41b.

The ultrasound transducer array 61 transmits and receives ultrasound in a range of a predetermined angle $\theta 2$ along a convex surface as shown in FIG. 3. The ultrasound transducer array 61 has an ultrasound scanning surface Z parallel to the insertion axis X.

The ultrasound transducer array 61 is provided so that a surface thereof protrudes beyond an edge line R connecting an edge peak A on a distal end side of the one surface 43 facing a direction perpendicular to the insertion axis X of the distal end portion 6 and an outline peak B of the distal end portion 6. The outline peak B is one point of a maximum diameter portion of the distal end portion 6 in a direction of the scanning surface Z of the ultrasound transducer array 61. Further, the ultrasound transducer array 61 is provided so that the surface thereof does not protrude beyond an outline of the distal end portion 6.

Thus, with the endoscope 2, the ultrasound transducer array 61 can be easily brought into reliable contact with a living body to provide satisfactory ultrasound images, without an auxiliary function for providing ultrasound images such as a balloon which has been used. Along with such a configuration, the ultrasound transducer array 61 is provided so as not to protrude beyond the outline of the distal end portion 6 of the endoscope 2, thereby preventing an increase in diameter of the endoscope 2 and providing satisfactory ultrasound images.

The second raising base 62 is pivotably provided in the second opening 41b. The second raising base 62 is pivoted by an operation of the raising lever 18 (see FIG. 1) provided in the operation portion 10. The second raising base 62 is pivoted in a raised direction to raise and guide a treatment instrument, for example, a puncture needle 101 protruded from the second treatment instrument channel 63 into the second opening 41b in the direction of the scanning surface Z of the ultrasound transducer array 61.

The second treatment instrument channel 63 is tilted so that a channel opening faces into the second opening 41b at a predetermined angle, and provided so that an extension line of a hole axis Y directed from the channel opening toward the scanning surface Z of the ultrasound transducer array 61 is included in the scanning surface Z.

Thus, with the endoscope 2, the treatment instrument such as the puncture needle 101 is displayed in an ultrasound image without the treatment instrument being raised by the second raising base 62, and an operator can perform a proper treatment operation without losing sight of the treatment instrument.

The second opening 41b in which the second raising base 62 is provided is located on a rear side of the distal end portion 6 along the insertion axis X with respect to the scanning surface Z of the ultrasound transducer array 61. Thus, the treatment instrument can be reliably guided out of the second opening 41b into the scanning surface Z of the ultrasound transducer array 61, and can be raised to a desired position in the scanning surface Z by the second raising base 62.

Next, configurations of the raising bases 53 and 62 will be described in detail with reference to FIGS. 5 to 7. The raising bases 53 and 62 have the same configuration.

As shown in FIGS. 5 to 7, each of the raising bases 53 and 62 includes a raising block 71, a frame 72 that pivotably supports the raising block 71, a rigid tube member 73 extending from a rear of the frame 72, a coil tube 74 connected to the tube member 73 and extending to the operation portion 10 (see FIG. 1) and around which a metallic wire is tightly wound, and an operation wire 75 passing through the raising block 71 and inserted through the coil tube 74 from the frame 72. The rigid tube member 73 and the coil tube 74 of each of the raising bases 53 and 62 are provided along the insertion axis X.

A recess 71a that guides a treatment instrument is formed in an upper surface of the raising block 71. The operation wires 75 of the raising bases 53 and 62 are connected to the two raising levers 17 and 18 (see FIG. 1), respectively, provided in the operation portion 10.

When each of the raising levers 17 and 18 is operated, the operation wire 75 is pulled or loosened. When the operation wire 75 is pulled, as shown in FIGS. 6 and 7, the raising block 71 pivotably supported by the frame 72 is pivoted so as to be pulled rearward and raised.

As such, treatment instruments inserted through the treatment instrument channels 54 and 63 are guided out of the openings 41a and 41b in the distal end portion 6 along the recess 71a in the raising block 71, and raised in a direction desired by the operator.

As shown in FIG. 8, the first raising base 53 may be operated pivotably around a longitudinal axis of the tube member 73 of the frame 72 and the coil tube 74, that is, an axis along the insertion axis X. With such a configuration, the treatment instrument such as the contrast tube 100 extended from the first opening 41a is tilted into the scanning surface Z of the ultrasound transducer array 61, thereby allowing optical observation and also ultrasound observation. Such a configuration can be, of course, also applied to the second raising base 62.

From the above, with the endoscope 2 of the present embodiment, in both procedures of endoscopic retrograde cholangiopancreatography (ERCP) and endoscopic ultrasound-guided fine needle aspiration biopsy (FNA), protruding directions of the treatment instruments from the distal end portion 6 of the endoscope 2 can be finely adjusted by the raising bases 53 and 62 to increase insertion performance of a treatment instrument for duodenal papilla, herein the contrast tube 100, and puncture performance of a treatment instrument for tissue for puncture, herein the puncture needle 101.

As described above, in the endoscopic ultrasound system 1 of the present embodiment, the distal end portion 6 of the endoscope 2 includes the optical observation function unit 50 including the optical observation system for optical observation of a subject and the raising base 53, and the ultrasound observation function unit 60 including the ultrasound transducer array 61 for ultrasound observation of the subject and the raising base 62. Thus, the endoscopic ultrasound system 1 can alone perform endoscopic retrograde cholangiopancreatography (ERCP) and endoscopic ultrasound-guided fine needle aspiration biopsy (FNA).

Thus, when it is expected that there is an abnormality in cells of a subject after endoscopic retrograde cholangiopancreatography (ERCP) with the endoscope 2 of the endoscopic ultrasound system 1, the operator can immediately perform endoscopic ultrasound-guided fine needle aspiration biopsy (FNA). Specifically, unlike conventional cases, the operator does not need to remove an insertion portion of an endoscope used for endoscopic retrograde cholangiopancreatography (ERCP) from an inside of a body cavity of a patient, and inserting an insertion portion of an endoscope used for endoscopic ultrasound-guided fine needle aspiration biopsy (FNA) into the body cavity, thereby reducing an operation time without placing an unnecessary burden on a patient, and significantly facilitating a procedure.

Further, the endoscope 2 can alone perform endoscopic retrograde cholangiopancreatography (ERCP) and endoscopic ultrasound-guided fine needle aspiration biopsy (FNA), thereby reducing costs. Also, only one time washing and sterilization of the endoscope 2 is necessary, thereby simplifying sanitation control.

With the endoscope 2 of the present embodiment, the optical observation function unit 50 is provided on the distal end side of the ultrasound observation function unit 60 in the distal end portion 6, and thus the bending portion 7 is operated in a bending manner so that the optical observation function unit 50 is brought close to duodenal papilla to allow close observation of the papilla during endoscopic retrograde cholangiopancreatography (ERCP), and also a distance between the first opening 41a and the papilla can be reduced to increase insertion performance of the treatment instrument into the papilla.

According to the present invention, an endoscope apparatus can be achieved that alone can perform endoscopic retrograde cholangiopancreatography (ERCP) and endoscopic ultrasound-guided fine needle aspiration biopsy (FNA), and thus can reduce a burden on a patient, does not trouble an operator with a complicated procedure, can reduce an operation time, and further can reduce introduction costs for a hospital and the number of times of washing and sterilization to facilitate sanitation control.

The invention described in the present embodiment is not limited to the embodiment and the variant, and various modifications may be made without departing from the gist of the invention in implementation stages. The present embodiment includes various stages of invention, and various kinds of invention can be derived by combinations of a plurality of disclosed constituent elements.

For example, when the problems described in Problems to be Solved by the Invention can be solved and the advantage described in Advantage of the Invention can be obtained even if several constituent elements are deleted from all constituent elements disclosed in the embodiment, a configuration with the constituent elements being deleted can be derived as an invention.

What is claimed is:

1. An ultrasound endoscope comprising:
an insertion portion adapted to be inserted into a subject along an insertion axis;
an ultrasound transducer array which is provided at the insertion portion and transmits and receives ultrasound;
a first channel opening which is an opening provided at the insertion portion and arranged to be distal or proximal with respect to the ultrasound transducer array; and
a first raising base which is arranged inside the first channel opening for adjusting a guiding direction of a treatment instrument guided out of the first channel opening;
wherein the first raising base includes:
a raising block which guides the treatment instrument, a frame which is provided in a distal end rigid portion of a distal end portion and pivotally supports the raising block, a tube member which extends from a rear of the frame and rotates around an insertion axis to thereby rotate the raising block in a first direction around an axis along the insertion axis, and a wire which is connected to the raising block and causes the raising block to be raised in a second direction around an axis perpendicular to the insertion axis by advancing and retreating in the insertion direction, and wherein the first raising base causes the treatment instrument to be tilted in the first direction and also causes the treatment instrument to be raised in the second direction around the axis perpendicular to the insertion axis.

2. An ultrasound endoscope according to claim 1, further comprising an optical observation system provided at the insertion portion and arranged at a lateral position of the first channel opening.

3. An ultrasound endoscope according to claim 1, further comprising a second channel opening which is an opening provided at the insertion portion, the second channel opening being arranged on a side opposite to the first channel opening with the ultrasound transducer array therebetween.

4. An ultrasound endoscope according to claim 3, further comprising a second raising base which is arranged inside the second channel opening for adjusting a guiding direction of a treatment instrument guided out of the second channel opening.

* * * * *